(12) United States Patent
Hatori (10) Patent No.: US 7,409,130 B2
(45) Date of Patent: Aug. 5, 2008

(54) ENDOSCOPE

(75) Inventor: Tsuruo Hatori, Sagamihara (JP)

(73) Assignee: Olympus Corporation, Tokyo (JP)

( * ) Notice: Subject to any disclaimer, the term of this patent is extended or adjusted under 35 U.S.C. 154(b) by 2 days.

(21) Appl. No.: 10/966,373

(22) Filed: Oct. 15, 2004

(65) Prior Publication Data
US 2005/0089286 A1  Apr. 28, 2005

(30) Foreign Application Priority Data
Oct. 16, 2003  (JP)  ............... 2003-356532

(51) Int. Cl.
*G02B 6/06* (2006.01)
(52) U.S. Cl. ................................ 385/117; 385/118
(58) Field of Classification Search ................ 385/117, 385/118
See application file for complete search history.

(56) References Cited

U.S. PATENT DOCUMENTS 5,621,830 A * 4/1997 Lucey et al. ............... 385/25

2002/0186478 A1  12/2002 Watanabe et al.

FOREIGN PATENT DOCUMENTS

| EP | 0 072 205 | 2/1983 |
| EP | 0 978 251 A1 | 2/2000 |
| JP | 57-31832 | 2/1982 |
| JP | 5-887 | 1/1993 |
| JP | 9-168505 | 6/1997 |
| JP | 9-234183 | 9/1997 |
| JP | 2002-85326 | 3/2002 |

* cited by examiner

*Primary Examiner*—Jennifer Doan
(74) *Attorney, Agent, or Firm*—Scully, Scott, Murphy & Presser, P.C.

(57) ABSTRACT

An endoscope includes an elongated insertion section which has a distal end portion and is inserted into a body cavity. The insertion section has a rigid portion body on the distal end portion. The rigid portion body has at least one mounting hole in which each of optical members of an observation optical system and an illumination optical system is mounted. A binding portion which mechanically restricts the optical member with respect to the rigid portion body is provided on at least a part of the boundary between the mounting hole and the optical member mounted in the mounting hole.

22 Claims, 6 Drawing Sheets

ENDOSCOPE

CROSS-REFERENCE TO RELATED APPLICATIONS

This application is based upon and claims the benefit of priority from prior Japanese Patent Application No. 2003-356532, filed Oct. 16, 2003, the entire contents of which are incorporated herein by reference.

BACKGROUND OF THE INVENTION

1. Field of the Invention

The present invention relates to an endoscope in which a rigid portion body on the distal end portion of an elongated insertion section to be inserted into a body cavity has mounting holes in which optical members of an observation optical system and an illumination optical system are mounted.

2. Description of the Related Art

In Jpn. Pat. Appln. KOKAI Publication No. 2002-85326, for example, a technique is described for fixing an optical member to a cover member that is provided independently of a rigid portion body on the distal end portion of an insertion section of an endoscope. According to this technique, the cover member having an opening is located on the distal end portion of the insertion section to hold the distal end face of the optical member in an exposed state. The diameter of the opening of the cover member on its one side is larger than the diameter on the other side, that is, the opening is tapered. The surface of the cover member which has the larger opening diameter is opposed to the proximal end side of the insertion section. The optical member has a tapered shape such that it is mounted in the tapered opening. Thus, the optical member can be prevented from slipping off the cover member.

The rigid portion body of the endoscope described above is formed having an opening in which an integrated unit that combines the optical member and a frame on the distal end portion of the insertion section is located. The optical member is firmly soldered or brazed to the frame. The cover member has a small hole in its distal end face. The diameter of the small hole is less than the largest diameter of the integrated unit. A large hole having a larger diameter than that of the small hole is formed in a position a little closer to the proximal end side of the insertion section than the distal end face of the cover member. The small and large holes are tapered and linked together. The optical member of the unit is tapered to mount the tapered cover member. If the integrated unit is inserted into the cover member from its proximal end side and fixed the optical member is prevented from being disengaged in a forward direction from the distal end face of the cover member.

BRIEF SUMMARY OF THE INVENTION

According to an aspect of the present invention, there is provided an endoscope including an elongated insertion section which has a distal end portion and is inserted into a body cavity. The insertion section has a rigid portion body on the distal end portion. The rigid portion body has at least one mounting hole in which each of optical members of an observation optical system and an illumination optical system is mounted. A binding portion which mechanically restricts the optical member with respect to the rigid portion body is provided on at least a part of the boundary between the mounting hole and the optical member mounted in the mounting hole.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the embodiments given below, serve to explain the principles of the invention.

DETAILED DESCRIPTION OF THE INVENTION

Several embodiments of the invention will now be described with reference to the accompanying drawings.

A first embodiment will first be described with reference to FIGS. 1 to 2C.

Figure 1:
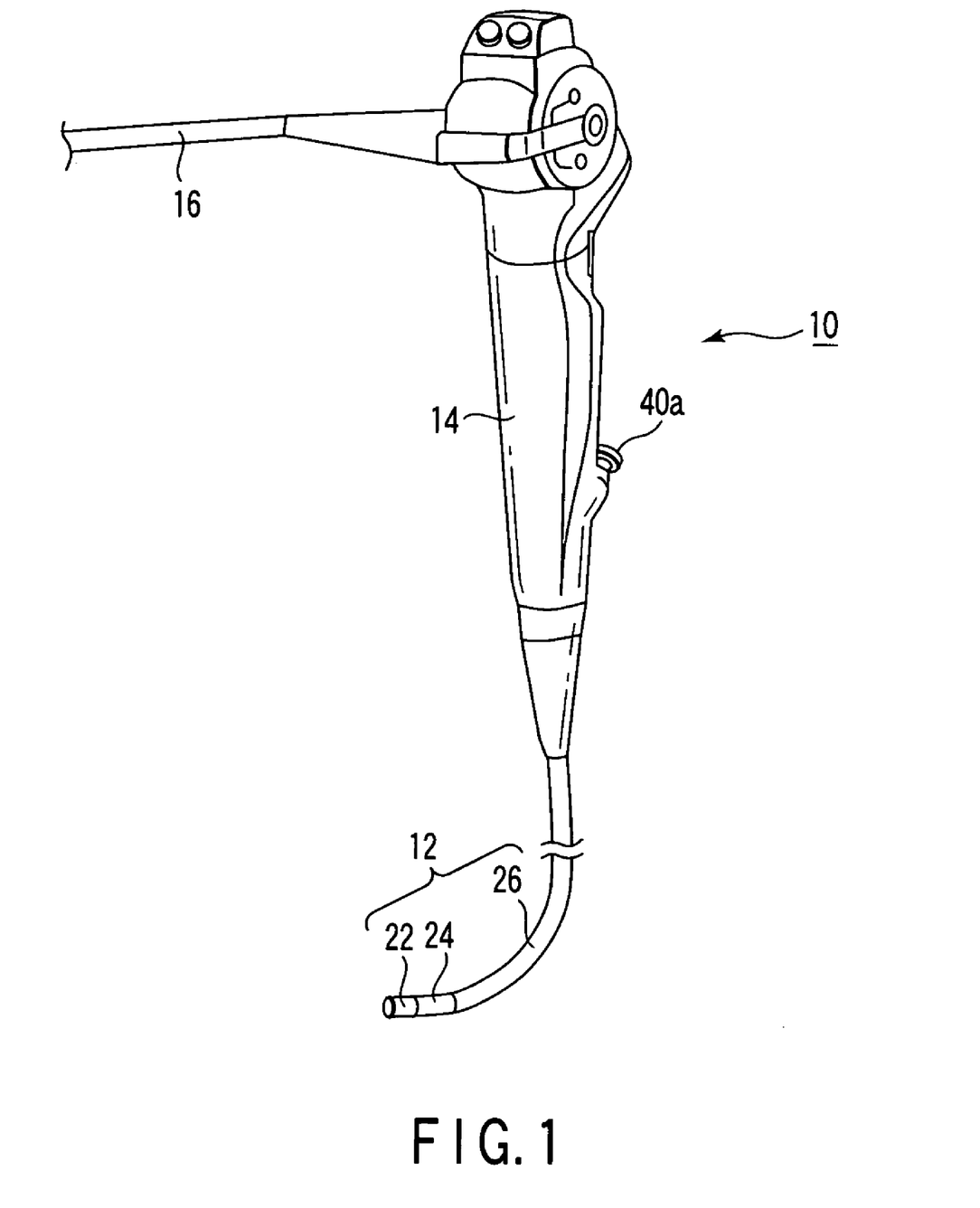
FIG. 1 is a schematic perspective view showing a configuration of an endoscope according to a first embodiment.

As shown in FIG. 1, an endoscope 10 according to the embodiment includes an elongated insertion section 12, which can be inserted into a body cavity, and an operation section 14 on the proximal end portion of the insertion section 12. The insertion section 12 has a rigid portion 22, a bending portion 24, and a flexible tube 26. The rigid portion 22 is located on the distal end portion of the insertion section 12. The bending portion 24 is provided on the proximal end portion of the rigid portion 22 and can be bent in a desired direction by manipulating the operation section 14. The flexible tube 26 has its distal and proximal end portions coupled to the proximal end portion of the bending portion 24 and the operation section 14, respectively.

Figure 2A:
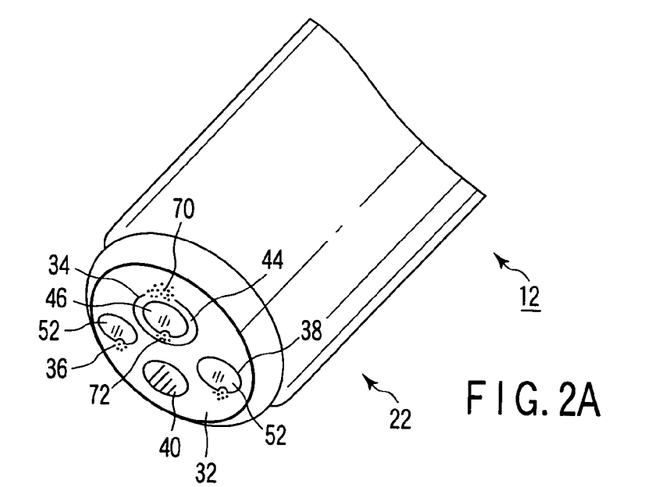
FIG. 2A is a schematic perspective view of the distal end portion of an insertion section of the endoscope according to the first embodiment.

As shown in FIG. 2A, the rigid portion 22 includes a rigid portion body 32. The body 32 is formed of a stainless steel material or the like that is a chemically stable metal material. The body 32 is formed having, for example, first to fourth circular holes 34, 36, 38 and 40 that extend parallel to the axial direction of the insertion section 12. As shown in FIG. 2A, an optical member is located in each of the first to third holes 34, 36 and 38. More specifically, an observation optical system is located as an optical member in the first hole 34, and illumination optical systems are arranged in the second and third holes 36 and 38, individually.

Figure 2B:
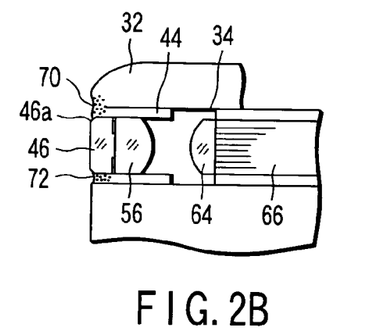
FIG. 2B is a schematic longitudinal sectional view showing a part of an observation optical system mounted in a rigid portion on the distal end portion of the insertion section of the endoscope according to the first embodiment.

As shown in FIGS. 2A and 2B, the outer peripheral surface of a cylindrical frame member 44 is in contact with the inner peripheral surface of the first circular hole 34. The former is bonded to the latter with an adhesive. The frame member 44 is formed of a stainless steel material or the like that is a chemically stable metal material. A substantially disc-shaped objective cover lens 46 for use as an optical window member is mounted in the frame member 44. The lens 46 is bonded to the frame member 44 with the adhesive.

Figure 2C:
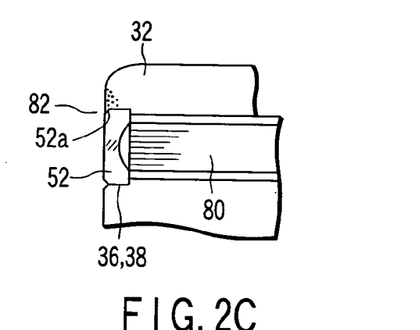
FIG. 2C is a schematic longitudinal sectional view showing a part of an illumination optical system mounted in the rigid portion on the distal end portion of the insertion section of the endoscope according to the first embodiment.

As shown in FIGS. 2A and 2C, a substantially disc-shaped illumination lens 52 for use as an optical window member is mounted in the inner peripheral surface of each of the second and third circular holes 36 and 38. The illumination lens 52 and the rigid portion body 32, like the objective cover lens 46 and the frame member 44, are bonded to each other with the adhesive.

The fourth circular hole 40 shown in FIG. 2A is formed as an opening portion on one end side of a channel through which an instrument (not shown) or the like is passed from the side of the operation section 14. More specifically, the hole 40 communicates with the interior of the insertion section 12, an opening portion 40a (see FIG. 1) on the other end side opens in the operation section 14. If necessary, the instrument or the like may be passed through the channel via the opening portion 40a of the operation section 14 and projected from the fourth first hole 40, or water (liquid) or air (gas) may be fed into a patient's body through the channel.

As shown in FIG. 2A, the objective cover lens 46, which is situated ahead of a group of objective lenses of the observation optical system, and the illumination lenses 52 of the illumination optical systems are exposed from the distal end face of the rigid portion body 32. The lenses 46 and 52 and other lenses are formed of a stable material, such as glass or sapphire.

A constriction is formed on the proximal end face of the objective cover lens 46 by etching or the like. As shown in FIG. 2B, a first convex lens 56 is affixed to the proximal end face of the lens 46 with a transparent adhesive in a manner such that it is convex toward the proximal end of the rigid portion body 32. The lenses 46 and 56 are mounted in a body in the pipe-shaped frame member 44. The outer peripheral surface of a member that integrally combines the lenses 46 and 56 and the inner peripheral surface of the frame member 44 are bonded to each other with the adhesive.

As shown in FIG. 2B, a chamfer portion 46a is formed on at least a part of the outer edge of the objective cover lens 46 on its distal end side. It has a regular size such that the peripheral edge of the lens 46 cannot be burred or chipped by manipulation.

The unitized member that combines the objective cover lens 46 and the first convex lens 56 mounted in the frame member 44 is bonded to the first circular hole 34 of the rigid portion body 32 with the adhesive. An image guide fiber 66 is passed through the first hole 34 of the body 32 on the proximal end side of the first convex lens 56. The outer peripheral surface of the fiber 66 is bonded to the inner peripheral surface of the first circular hole 34 with the adhesive. A second convex lens 64, which is convex toward the distal end portion of the rigid portion body 32, is affixed to the distal end face of the image guide fiber 66.

A part of the boundary between the peripheral edge of the distal end portion of the frame member 44 and the peripheral edge of the distal end portion (opening portion) of the first circular hole 34 of the rigid portion body 32 is spot-welded by irradiation with laser light or the like. The spot welding forms a fixing portion (weld portion) 70 in which a part of the boundary between the peripheral edge of the distal end portion of the frame member 44 and the peripheral edge of the distal end portion of the first circular hole 34 is fixed or bound. Thus, the frame member 44 and the rigid portion body 32 are jointed (or deposited) together by welding.

On the other hand, a part of the peripheral edge of the distal end portion of the frame member 44 is melted by irradiation with laser light (spot irradiation). The melted frame member 44 or molten metal is poured onto the chamfer portion 46a of the objective cover lens 46. A holding portion (weld portion) 72 is formed when the molten metal that is poured onto the chamfer portion 46a is set. The holding portion 72 serves to prevent the objective cover lens 46 from moving beyond the distal end of the frame member 44 to the distal end side.

Thus, the holding portion (binding portion) 72 restrains the objective cover lens 46 from moving forward beyond the distal end of the rigid portion body 32. The fixing portion (binding portion) 70 restrains the frame member 44 from moving forward beyond the body 32.

In this case, the holding portion 72 is set so as not to interfere with a light beam that forms an endoscopic image on the end face of the image guide fiber 66. However, the holding portion 72 may interfere with the light beam to a practicably allowable extent.

Like the objective cover lens 46 shown in FIG. 2B, each illumination lens 52 has a chamfer portion 52a formed on a part of its outer edge, as shown in FIG. 2C. The lens 52 is bonded to the second and third circular hole 36 and 38 of the rigid portion body 32 with the adhesive. One end face of a light guide fiber 80 abuts against the proximal end face of the lens 52. The fiber 80 is passed through the insertion section 12 of the endoscope 10, covering its overall length. The other end of the fiber 80 is connected to an optical source (not shown). Thus, light from the light source is guided from the other end of the fiber 80 to the distal end, and the light guide by the fiber 80 is emitted from the illumination lens 52 to irradiate a subject.

A part of the peripheral edge of the distal end portion (opening portion) of the second circular hole 36, like that of the frame member 44, is melted by irradiation with laser light, for example. The molten metal of the rigid portion body 32 is poured onto the chamfer portion 52a of each illumination lens 52. A holding portion (binding portion) 82 is formed when the molten metal that is poured onto the chamfer portion 52a is set. The holding portion 82 serves to prevent the illumination lens 52 from moving beyond the rigid portion body 32 to the distal end side by welding.

In this case, the holding portion 82 is adjusted to a size such that it does not interfere with illumination light emitted from the light guide fiber 80. The holding portion 82 may interfere with the illumination light to a practicably allowable extent.

In the embodiment, the one fixing portion 70 for the first circular hole 34 is provided on the peripheral edge of the frame member 44. Alternatively, the fixing portion 70 may be provided covering the entire circumference. Further, another fixing portion (not shown) may be located opposite the one fixing portion 70 to form a double fixed-point joint, or the peripheral edge of the frame member 44 may be divided into three equal sectors to form three fixing portions. Thus, the fixing portions are not limited in number. This also applies to the holding portion 72 of the objective cover lens 46 of the observation optical system and the holding portion 82 of the illumination lens 52 of each illumination optical system.

The following is a description of assembly operation for the rigid portion 22 at the distal end portion of the insertion section 12 of the endoscope 10 according to the embodiment.

In the initial stage of this operation, the rigid portion 22 of the insertion section 12 of the endoscope 10 is assembled in the same manner as a conventional endoscope. The objective cover lens 46 and the first convex lens 56 are affixed to each other with the transparent adhesive. The respective outer peripheral surfaces of the lenses 46 and 56 are bonded to the inner peripheral surface of the frame member 44 with the adhesive for unification. Preferably, in this case, the distal end face of the frame member 44 should be substantially flush with the objective cover lens 46. Thus, the first convex lens 56 is convex toward the proximal end portion of the frame member 44.

The adhesive is applied to the outer peripheral surface of the outer peripheral surface of the frame member 44 and/or the inner peripheral surface of the first circular hole 34 of the integrated unit. The unit is mounted into the first circular hole 34 of the rigid portion body 32 from the distal end side of the body 32 toward the proximal end portion. The outer peripheral surface of the frame member 44 and the inner peripheral surface of the first circular hole 34 are bonded to each other with the adhesive.

The adhesive is applied to the outer peripheral surface of one of the illumination lenses 52 and/or the second circular hole 36. The adhesive is also applied to the outer peripheral surface of the other illumination lens 52 and/or the third circular hole 38. The illumination lenses 52 are mounted individually into the second and third holes 36 and 38 of the rigid portion body 32 from the distal end side of the body 32 toward the proximal end portion. The outer peripheral surface of the one illumination lens 52 and the inner peripheral surface of the second circular hole 36 are bonded to each other with the adhesive. The outer peripheral surface of the other illumination lens 52 and the inner peripheral surface of the third circular hole 38 are bonded to each other with the adhesive.

Since these processes are independent of one another, they may naturally be replaced in the order of execution.

After the frame member 44 is bonded to the rigid portion body 32, laser light is applied to a given position on the distal end portion of the frame member 44 by spot irradiation. The spot welding forms the fixing portion 70 in which the peripheral edge of the distal end portion of the frame member 44 and that of first circular hole 34 of the rigid portion body 32 are fixed to each other. The position to which the laser light is applied is situated as close to the outer peripheral surface of the frame member 44 as possible. By doing this, the laser light can be prevented from influencing the objective cover lens 46, the first convex lens 56, etc.

Likewise, laser light is applied to the distal end portion of the frame member 44 by spot irradiation. Thereupon, an irradiated part of the distal end portion of the frame member 44 is melted instantly. The resulting molten metal of the frame member 44 is poured onto the chamfer portion 46a of the objective cover lens 46. The molten metal on the objective cover lens 46 is set to form the holding portion 72 (see FIG. 2B).

Likewise, after the illumination lens 52 is bonded to the rigid portion body 32, laser light is applied to a given position on the peripheral edge portion of the second circular hole 36 by spot irradiation. Thus, the peripheral edge portion of the second circular hole 36 is melted instantly. The resulting molten metal of the peripheral edge portion is poured onto the chamfer portion 52a of the lens 52. The molten metal on the chamfer portion 52a is set to form the holding portion 82 (see FIG. 2C).

In the embodiment, the spot irradiation with laser light has been described as welding or melting means. However, it may be replaced with any other welding or melting means that can pointedly heat an object instantly.

The endoscope 10 constructed in this manner sometimes may be cleaned, disinfected, or sterilized by some means that are not recommended by endoscope manufacturers. The objective cover lens 46 and the illumination lenses 52 of the endoscope 10 according to the embodiment are held to the rigid portion body 32 by the fixing portion 70, holding portions 72 and 82, etc. Thus, the lenses 46 and 52 are restricted and prevented by the fixing portion 70 and the holding portions 72 and 82 from moving forward with respect to the rigid portion body 32. In consequence, the lenses 46 and 52 can be prevented from coming off the rigid portion 22 of the insertion section 12 during use.

Thus, the endoscope 10 according to the embodiment provides the following effects.

If the frame member 44 and the objective cover lens 46 are disengaged from the body 32 of the rigid portion 22 of the insertion section 12 of the endoscope 10, owing to unexpected processing after use of the endoscope 10, the lens 46 can be kept held in the frame member 44 by the holding portion 72. The fixing portion 70 and the holding portion 72 can prevent the frame member 44 and the objective cover lens 46 from moving forward from the rigid portion body 32. Thus, the objective cover lens 46 and the first convex lens 56 can be prevented from slipping off the body 32 of the rigid portion 22 of the insertion section 12.

Since the objective cover lens 46 and the first convex lens 56 are attached to the rigid portion body 32 when the fixing portion 70 and the holding portion 72 are formed, assembly can be performed efficiently.

If the illumination lenses 52 are disengaged from the body 32 of the rigid portion 22 of the insertion section 12 of the endoscope 10, owing to unexpected processing after use of the endoscope 10, the holding portion 82 can prevent each illumination lens 52 from moving forward from the rigid portion body 32. Thus, the illumination lenses 52 can be prevented from slipping off the body 32 of the rigid portion 22 of the insertion section 12. Since each illumination lens 52 is attached to the rigid portion body 32 when the holding portion 82 is formed, moreover, assembly can be performed efficiently.

A second embodiment will now be described with reference to FIG. 3. The embodiment is a modification of the first embodiment. Therefore, like numerals are used to designate like members of the first and second embodiments, and a detailed description of those members will be omitted in the following.

In the first embodiment, the holding portion (weld portion) 72 is formed by spot-irradiating a part of the distal-side peripheral edge of the frame member 44 with laser light to melt it. In the second embodiment, a frame member 44 is provided with a constricted portion 90, which is formed by previously making the inside diameter of the distal end portion of the frame member 44 smaller than that of its proximal end portion, as shown in FIG. 3. The frame member 44 of the embodiment is more complicated in shape than the cylindrical frame member 44 of the first embodiment. However, the complicated shape derives only from the addition of the constricted portion 90.

In contrast with the case of the foregoing first embodiment, an objective cover lens 46 and a first convex lens 56, which are affixed to each other, are mounted into the frame member 44 from its proximal end side toward the constricted portion 90 at the distal end portion. The objective cover lens 46 is bonded to the constricted portion 90 at the distal end portion with an adhesive.

Figure 3:
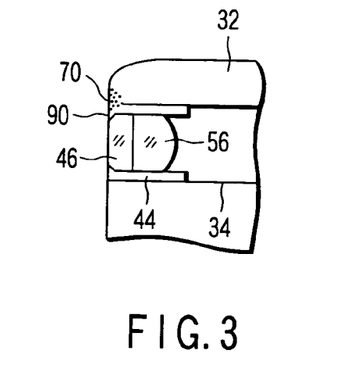
FIG. 3 is a schematic longitudinal sectional view showing a part of an observation optical system at the distal end portion of an insertion section of an endoscope according to a second embodiment.

If the frame member 44 has the shape shown in FIG. 3, the holding portion 72 (see FIGS. 2A and 2B) for the objective cover lens 46 need not be formed by melting a part of the distal end face of the frame member 44 with heat. Thus, thermal load on the objective cover lens 46 can be reduced to prevent cracking of the lens 46 or generation of residual stress.

A third embodiment will now be described with reference to FIG. 4. The embodiment is a modification of the first and second embodiments. Therefore, like numerals are used to designate like members of the first to third embodiments, and a detailed description of those members will be omitted in the following.

Figure 4:
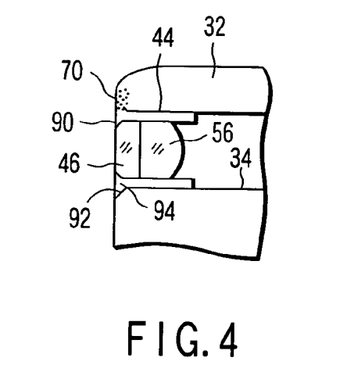
FIG. 4 is a schematic longitudinal sectional view showing a part of an observation optical system at the distal end portion of an insertion section of an endoscope according to a third embodiment.

FIG. 4 shows an arrangement for reducing thermal load on the objective cover lens 46. Like the constricted portion 90 formed on the frame member 44 of the second embodiment shown in FIG. 3, a constricted portion 90 is formed on the inner peripheral surface of the distal end portion of the frame member 44. A spread portion 92 is formed on the outer peripheral surface of the distal end portion of the frame member 44. Outside diameter of the spread portion 92 increases toward the distal end, and inside diameter of the spread portion 92 decreases. A spot-faced portion 94 is formed on a part of the peripheral edge portion of a first circular hole 34 of a first circular hole 34. The spot-faced portion 94 houses the spread portion 92.

The frame member 44 is fixed to the rigid portion body 32 by being melted by spot irradiation with laser light. In this case, the position of laser light irradiation is situated between the edge portion of the spot-faced portion 94 and that part of the peripheral edge of the spread portion 92 which is located at a distance from the center of the first circular hole 34. If the portion to be melted by heating is kept apart from the objective cover lens 46, thermal load on the lens 46 can be reduced.

A fourth embodiment will now be described with reference to FIGS. 5A to 5C. The embodiment is a modification of the first to third embodiments. Therefore, like numerals are used to designate like members of the first to fourth embodiments, and a detailed description of those members will be omitted in the following.

Figure 5A:
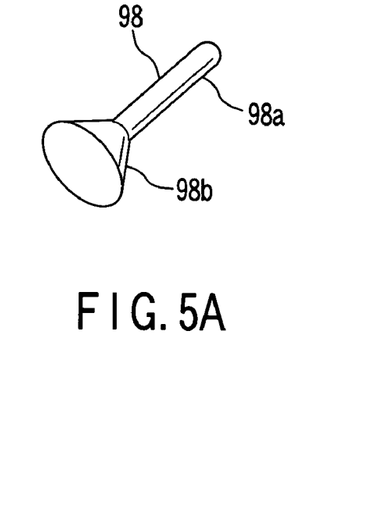
FIG. 5A is a schematic perspective view showing a fixing pin to be located in the distal end portion of an insertion section of an endoscope according to a fourth embodiment.
Figure 5B:
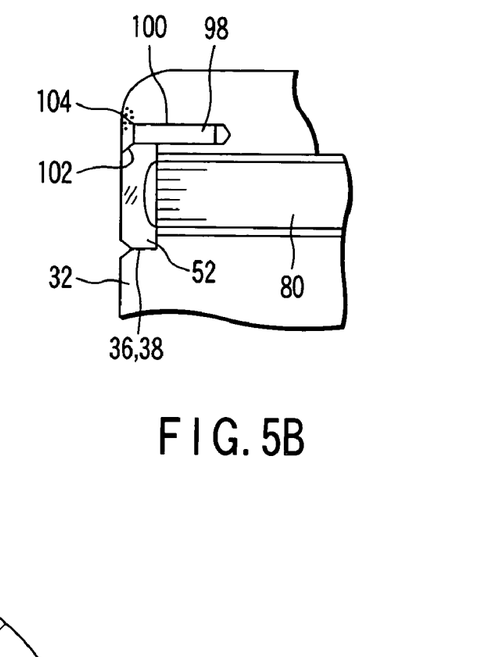
FIG. 5B is a schematic longitudinal sectional view showing a part of an observation optical system at the distal end portion of the insertion section of the endoscope according to the fourth embodiment.
Figure 5C:
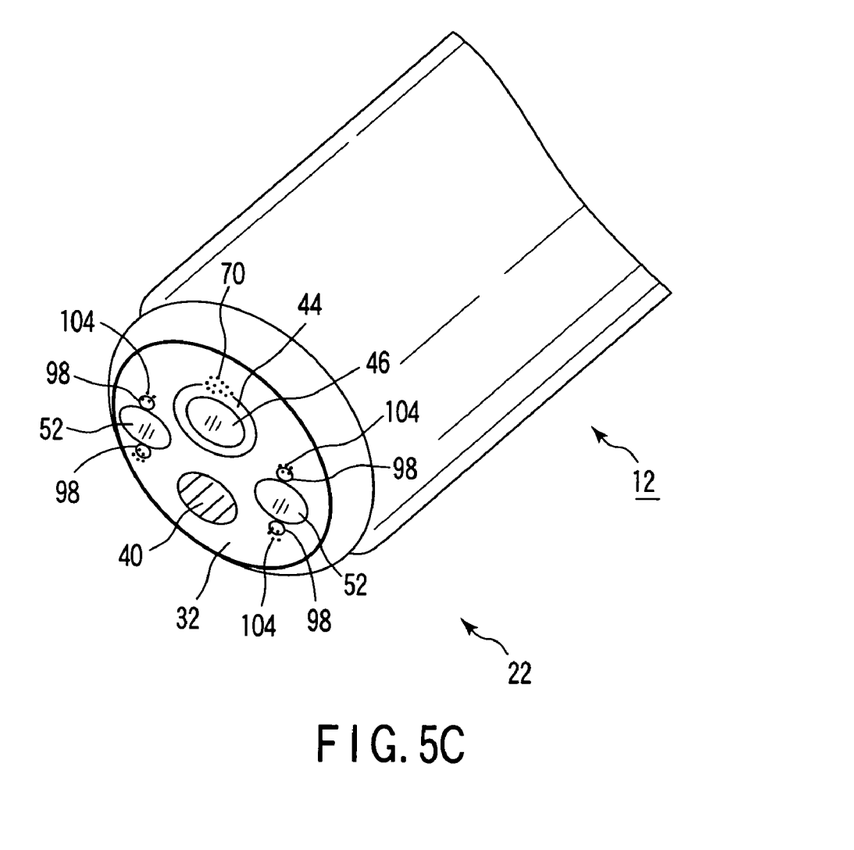
FIG. 5C is a schematic perspective view of the distal end portion of the insertion section of the endoscope according to the fourth embodiment.

FIGS. 5A to 5C show an arrangement for reducing thermal load on illumination lenses 52. The lenses 52 use no frame member like the illumination lenses according to the first embodiment.

FIG. 5A shows a fixing pin 98. The fixing pin 98 includes a columnar portion 98a in the form of a short, thin rod and a spread portion 98b that protrudes integrally from one end portion of the columnar portion 98a.

As shown in FIG. 5B, a rigid portion body 32 is formed having adjacent holes 100 near second and third circular holes 36 and 38 that houses its illumination lenses 52, individually. Each hole 100 houses the fixing pin 98 shown in FIG. 5A. The diameter of the hole 100 is smaller than that of the holes 36 and 38.

After the illumination lenses 52 are mounted into and bonded to the second and third circular holes 36 and 38, the fixing pins 98 are inserted into the adjacent holes 100, individually. The pins 98 are bonded to the rigid portion body 32 with an adhesive. Thereupon, the spread portion 98b of each pin 98 is caught by the distal end face of each corresponding illumination lens 52 and forms a holding portion 102.

Thereafter, laser light is applied to the boundary between each adjacent hole 100 and the distal end face of the spread portion 98b that is situated farthest from the center of each illumination lens 52, as shown in FIGS. 5B and 5C. Thereupon, the rigid portion body 32 is pointedly melted to form fixing portions 104. Thus, the fixing pins 98 are fixed to the body 32.

In this case, the two fixing pins 98 are located opposite the illumination lenses 52, individually, as shown in FIG. 5C. It is to be understood, however, that the endoscope 10 may be provided with any number of fixing pins if its design affords spatial allowance.

A fifth embodiment will now be described with reference to FIGS. 6A to 6D. The embodiment is a modification of the first embodiment. Therefore, like numerals are used to designate like members of the first and fifth embodiments, and a detailed description of those members will be omitted in the following.

Figure 6A:
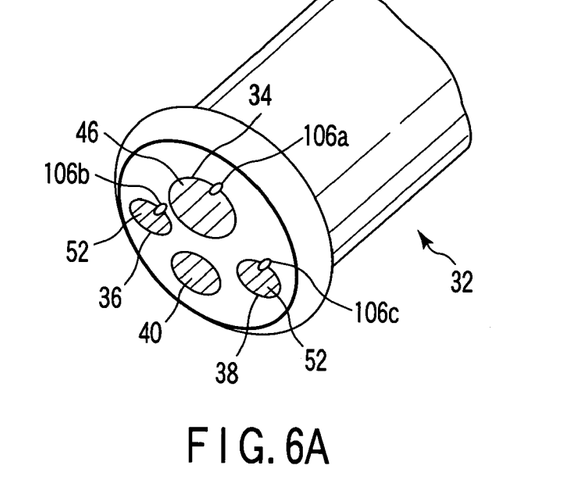
FIG. 6A is a schematic perspective view of a rigid portion body on the distal end portion of an insertion section of an endoscope according to a fifth embodiment.

FIG. 6A shows a rigid portion body 32 of an endoscope 10 according to the fifth embodiment. A fine first protrusion (worked portion) 106a is formed on a part of the peripheral edge of an opening of a first circular hole 34 in which an objective cover lens 46 is located. Likewise, second and third protrusions (worked portions) 106b and 106c are formed, respectively, on the peripheral edges of second and third circular holes 36 and 38 in which illumination lenses 52 are arranged, individually.

Figure 6B:
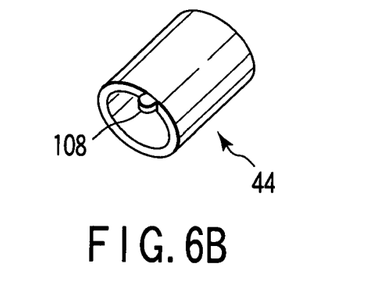
FIG. 6B is a schematic perspective view of a frame member to be located in the distal end portion of the insertion section of the endoscope according to the fifth embodiment.

FIG. 6B shows a frame member 44 that houses the objective cover lens 46 and a first convex lens 56. The frame member 44, like the rigid portion body 32, is formed having a protrusion (worked portion) 108 on its distal end side.

Figure 6C:
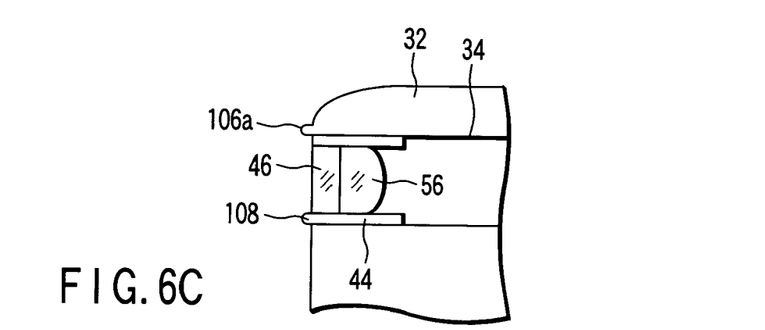
FIG. 6C is a schematic longitudinal sectional view showing a part of an observation optical system at the distal end portion of the insertion section of the endoscope according to the fifth embodiment.
Figure 6D:
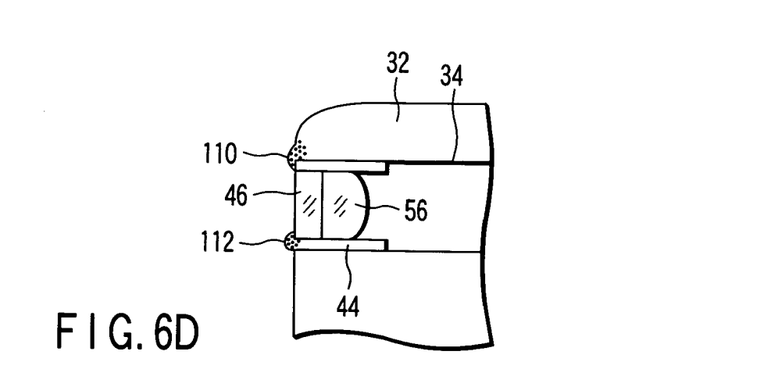
FIG. 6D is a schematic longitudinal sectional view showing a part of the observation optical system at the distal end portion of the insertion section of the endoscope according to the fifth embodiment.

FIG. 6C shows a state in which a unit that combines the objective cover lens 46 and the first convex lens 56 bonded together is incorporated in the frame member 44. FIG. 6D shows a state of the rigid portion body 32 and the integrated unit that combines the lenses 46 and 56 after the protrusions 106a and 108 are suitably spot-irradiated with laser light.

The protrusions 106a, 106b, 106c and 108 are heated and melted by spot irradiation with laser light. The first protrusion 106a is formed as a holding portion 110 for the frame member 44 and the rigid portion body 32. The protrusion 108 is formed as a holding portion 112 for the objective cover lens 46 and the frame member 44. As the second and third protrusions 106b and 106c are melted, holding portions 110 and 112 for the illumination lenses 52 and the rigid portion body 32 are formed individually. The protrusions 106a, 106b, 106c and 108 are formed having smooth surfaces owing to surface tension that is produced as they are melted.

Although the protrusions 106a, 106b, 106c and 108 are heated and melted with laser light to form the holding portions 110 and 112 according to the embodiment, the holding portions 110 and 112 may alternatively be formed by mechanically caulking the protrusions. If the mechanical caulking is employed, there is no need of any large-sized working apparatus, such as a laser welding apparatus.

Figure 7A:
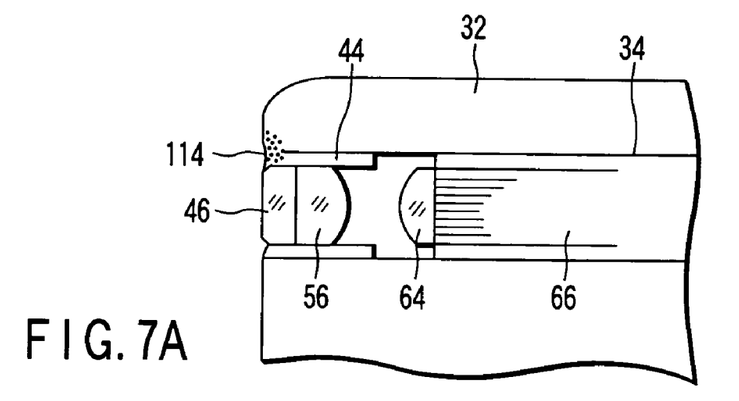
FIG. 7A is a schematic longitudinal sectional view showing a part of an observation optical system at the distal end portion of an insertion section of an endoscope according to a sixth embodiment.
Figure 7B:
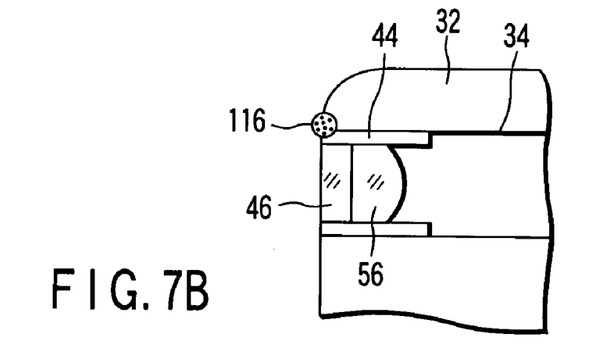
FIG. 7B is a schematic longitudinal sectional view showing a part of the observation optical system at the distal end portion of the insertion section of the endoscope according to the sixth embodiment.
Figure 7C:
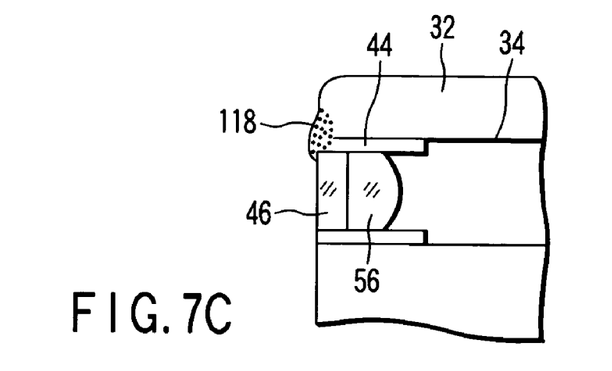
FIG. 7C is a schematic longitudinal sectional view showing a part of the observation optical system at the distal end portion of the insertion section of the endoscope according to the sixth embodiment.

A sixth embodiment will now be described with reference to FIGS. 7A to 7C. The embodiment is a modification of the first embodiment. Therefore, like numerals are used to designate like members of the first and sixth embodiments, and a detailed description of those members will be omitted in the following.

In the arrangement of the first embodiment shown in FIG. 2B before use of laser light, a frame member 44 is melted by spot-irradiating a part of its distal end face with laser light. As shown in FIG. 7A, molten metal of the melted frame member 44 that is run out forward from a rigid portion 22 is set. Thus, a weld portion 114 is formed that combines the functions of the fixing portion 70 and the holding portion 72 according to the first embodiment.

Thus, the weld portion 114 that doubles as the fixing portion 70 and the holding portion 72 can be formed by one cycle of laser irradiation. Accordingly, manufacturing processes can be simplified, so that cost can be reduced. While the position of irradiation must be settled before the laser light is applied, the positioning frequency can be reduced.

The weld portion 114 has been described above as being formed with use of the melted frame member 44 as a base material. Alternatively, however, it may be formed in the manner shown in FIGS. 7B and 7C. In this case, notches for a solder deposit 116 are suitably formed in advance in a rigid portion body 32 and the frame member 44, as shown in FIG. 7B. The weld portion 118 is formed by applying laser light to the deposit 116 in the notches, as shown in FIG. 7C.

A seventh embodiment will now be described with reference to FIGS. 8A to 9C. The embodiment is a modification of the first embodiment. Therefore, like numerals are used to designate like members of the first and seventh embodiments, and a detailed description of those members will be omitted in the following.

Figure 8A:
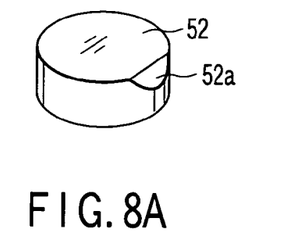
FIG. 8A is a schematic perspective view showing an illumination lens to be located in the distal end portion of an insertion section of an endoscope according to a seventh embodiment.
Figure 8B:
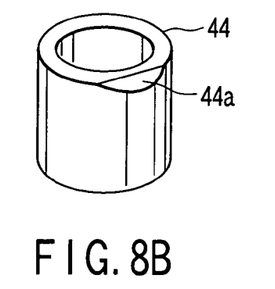
FIG. 8B is a schematic perspective view showing a frame member to be located in the distal end portion of the insertion section of the endoscope according to the seventh embodiment.

FIG. 8A shows an illumination lens 52 having a chamfer portion 52a formed on a part of its distal-side outer peripheral edge. Likewise, FIG. 8B shows a frame member 44 having a chamfer portion 44a formed on a part of its distal-side outer peripheral edge.

Figure 9A:
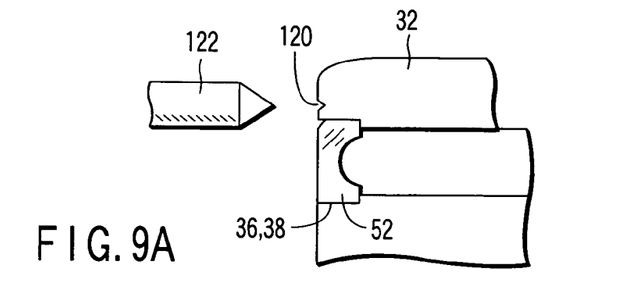
FIG. 9A is a schematic longitudinal sectional view showing a part of an illumination optical system in the distal end portion of the insertion section of the endoscope and illustrating a state before the illumination lens is caulked to a rigid portion body according to the seventh embodiment.
Figure 9B:
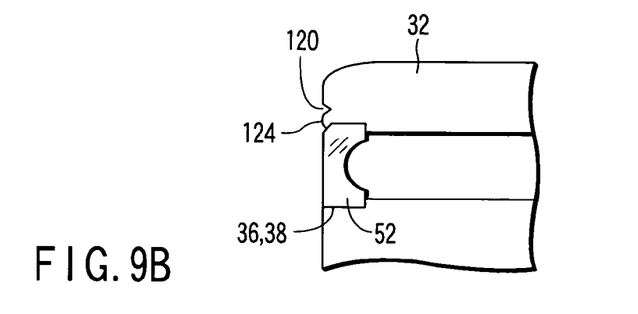
FIG. 9B is a schematic longitudinal sectional view showing a part of the illumination optical system in the distal end portion of the insertion section of the endoscope and illustrating a state after the illumination lens is caulked to the rigid portion body according to the seventh embodiment.

As shown in FIG. 9A, the illumination lens 52 is bonded to a rigid portion body 32 with an adhesive. A punch hole 120 is formed in the peripheral edge portion of each of second and third circular holes 36 and 38 (or near the circular holes 36 and 38 for illumination lenses 52) of the body 32 in which the illumination lens 52 is fixed.

A caulking tool 122 on the left-hand side of FIG. 9A is held and pressed against the punch hole 120. That part of the rigid portion body 32 which is held between the tool 122 and the chamfer portion 52a of the illumination lens 52 is plastically deformed to form a holding portion (worked portion) 124 shown in FIG. 9B.

Figure 9C:
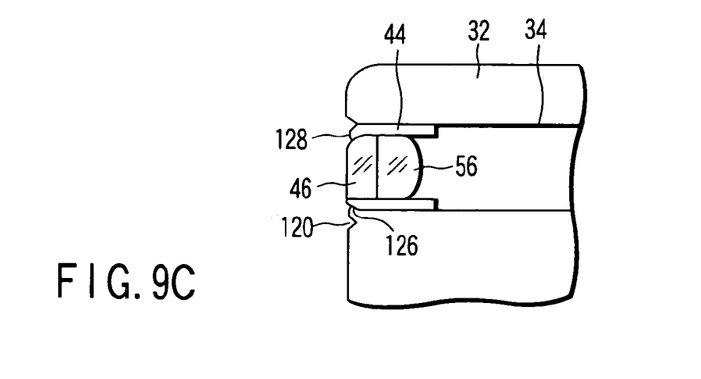
FIG. 9C is a schematic longitudinal sectional view showing a part of an observation optical system at the distal end portion of the insertion section of the endoscope according to the seventh embodiment.

FIG. 9C shows a state in which an objective cover lens 46 and a first convex lens 56 that constitute an objective optical system are held to the rigid portion body 32 by the frame member 44. The body 32 is partially deformed to be provided with a holding portion 126 for retaining the chamfer portion 44a of the frame member 44. The holding portion 126 is formed by the same processes as those for the holding portion 124 described with reference to FIGS. 9A and 9B.

A holding portion 128 is formed on the distal end portion of the frame member 44 so that the objective cover lens 46 with a chamfer portion 46a, like the illumination lens 52, can be held to the distal end portion of the frame member 44. The holding portion 128 is formed in the same manner as the constricted portion 90 (see FIG. 3) according to the second embodiment.

Thus, the objective cover lens 46, illumination lenses 52, and other lens can be prevented from slipping off the rigid portion body 32 without using any large-sized working apparatus, such as a laser apparatus.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
   an elongated insertion section which has a distal end portion and is inserted into a body cavity, the insertion section having a rigid portion body on the distal end portion, the rigid portion body having at least one mounting hole in which each of optical members of an observation optical system and an illumination optical system is mounted, a binding portion which mechanically restricts the optical member with respect to the rigid portion body is provided on at least a part of the boundary between the mounting hole and the optical member mounted in the mounting hole;

wherein the binding portion includes a holding portion which extends from the peripheral edge of an opening portion of the mounting hole toward the inside of the opening portion and retains the optical member and the holding portion includes a worked portion which is formed by machining the peripheral edge of the mounting hole and holds the optical member to the rigid portion body.

2. An endoscope according to claim 1, wherein the worked portion includes a protrusion which is provided on the peripheral edge of the opening portion of the mounting hole and is machined.

3. An endoscope comprising:
an elongated insertion section which has a distal end portion and is inserted into a body cavity, the insertion section having a rigid portion body on the distal end portion, the rigid portion body having at least one mounting hole in which each of optical members of an observation optical system and an illumination optical system is mounted, a binding portion which mechanically restricts the optical member with respect to the rigid portion body is provided on at least a part of the boundary between the mounting hole and the optical member mounted in the mounting hole;
wherein the binding portion includes a holding portion which extends from the peripheral edge of an opening portion of the mounting hole toward the inside of the opening portion and retains the optical member and the holding portion includes a worked portion which is formed by thermally processing the peripheral edge of the mounting hole and holds the optical member to the rigid portion body.

4. An endoscope comprising:
an elongated insertion section which has a distal end portion and is inserted into a body cavity, the insertion section having a rigid portion body on the distal end portion, the rigid portion body having at least one mounting hole in which each of optical members of an observation optical system and an illumination optical system is mounted, a binding portion which mechanically restricts the optical member with respect to the rigid portion body is provided on at least a part of the boundary between the mounting hole and the optical member mounted in the mounting hole;
wherein the binding portion includes a holding portion which extends from a part of the peripheral edge of an opening portion of the mounting hole toward the inside of the opening portion and fixes the optical member by at least one of mechanically, physically, and thermally deforming an edge portion of the opening portion of the mounting hole at a distal end face of the distal end portion.

5. An endoscope comprising:
an elongated insertion section which has a distal end portion and is inserted into a body cavity, the insertion section having a rigid portion body on the distal end portion, the rigid portion body having at least one mounting hole in which each of optical members of an observation optical system and an illumination optical system is mounted, a binding portion which mechanically restricts the optical member with respect to the rigid portion body is provided on at least a part of the boundary between the mounting hole and the optical member mounted in the mounting hole;
wherein the binding portion includes a fixing portion which extends from the peripheral edge of an opening portion of the mounting hole toward the inside of the opening portion and fixes the optical member and the fixing portion includes a weld portion which welds at least a part of the boundary between the optical member and the peripheral edge of the opening portion of the mounting hole.

6. An endoscope according to claim 5, wherein the weld portion includes an extended portion formed in a manner such that the rigid portion body and the optical member are fixed together by setting a molten metal formed by melting a part of the rigid portion body so that the molten metal extends from at least a part of the peripheral edge of the optical member.

7. An endoscope according to claim 5, wherein the optical member includes a cylindrical frame member, which is mounted in the inner peripheral surface of the mounting hole and melts when heated by heating means, and a lens mounted in the frame member.

8. An endoscope according to claim 7, wherein the heating means is laser light which pointedly heats an edge portion of the frame member from the side of the distal end portion of the insertion section.

9. An endoscope according to claim 7, wherein the weld portion includes an extended portion formed in a manner such that the rigid portion body and the optical member are fixed together by setting a molten metal formed by melting a part of the rigid portion body so that the molten metal extends from at least a part of the peripheral edge of the optical member.

10. An endoscope comprising:
an elongated insertion section which has a distal end portion and is inserted into a body cavity, the insertion section having a rigid portion body on the distal end portion, the rigid portion body having at least one mounting hole in which each of optical members of an observation optical system and an illumination optical system is mounted, a binding portion which mechanically restricts the optical member with respect to the rigid portion body is provided on at least a part of the boundary between the mounting hole and the optical member mounted in the mounting hole;
wherein the binding portion includes a fixing portion which extends from the peripheral edge of an opening portion of the mounting hole toward the inside of the opening portion and fixes the optical member and the binding portion includes a holding portion which extends from the peripheral edge of the opening portion of the mounting hole toward the inside of the opening portion and retains the optical member by at least one of mechanically, physically, and thermally deforming an edge portion of the opening portion of the mounting hole at a distal end face of the distal end portion.

11. An endoscope according to claim 10, wherein the mechanically deforming of the holding portion includes a worked portion which is formed by machining the peripheral edge of the mounting hole to hold the optical member to the rigid portion body.

12. An endoscope according to claim 11, wherein the worked portion includes a protrusion which is provided on the peripheral edge of the opening portion of the mounting hole and is machined.

13. An endoscope according to claim 10, wherein the mechanically deforming of the holding portion includes a worked portion which is formed by thermally processing the peripheral edge of the mounting hole to hold the optical member to the rigid portion body.

14. An endoscope comprising:
an elongated insertion section which has a distal end portion and is inserted into a body cavity, the insertion section having a rigid portion body on the distal end portion, the rigid portion body having at least one mounting hole in which each of optical members of an observation optical system and an illumination optical system is mounted, a binding portion which mechanically restricts the optical member with respect to the rigid portion body is provided on at least a part of the boundary between the mounting hole and the optical member mounted in the mounting hole;

wherein the binding portion includes a holding portion which has a holding pin, having a shaft portion and a head portion provided on one end portion of the shaft portion and larger in diameter than the shaft portion, and at least one small hole which is formed in the peripheral edge of the opening portion of the mounting hole and is smaller in diameter than the mounting hole and in which the shaft portion of the holding pin is inserted, such that a part of the head portion of the holding pin holds the peripheral edge portion of the optical member to the mounting hole.

15. An endoscope comprising:

an elongated insertion section which has a distal end portion and is inserted into a body cavity, the insertion section having a rigid portion body on the distal end portion, the rigid portion body having at least one mounting hole in which each of optical members of an observation optical system and an illumination optical system is mounted, a binding portion which mechanically restricts the optical member with respect to the rigid portion body is provided on at least a part of the boundary between the mounting hole and the optical member mounted in the mounting hole;

wherein the optical member includes an optical window member and a frame member which holds the optical window member, the binding portion has a fixing portion which fixes at least a part between the mounting hole and the frame member, a holding portion which holds the optical window member to the frame member and the fixing portion and the holding portion are formed integrally with each other, wherein at least one of the fixing portion and holding portion is formed by at least one of mechanically, physically, and thermally deforming an edge portion of the frame member at a distal end face of the distal end portion.

16. An endoscope comprising:

an elongated insertion section having a distal end portion, the insertion section having on the distal end portion thereof a rigid portion body which has a locating hole in which at least one of an objective optical system and an illumination optical system, each having an optical member, is located, a holding portion which extends from an edge portion of the locating hole and prevents the optical member from slipping off the locating hole is provided on the boundary between the optical member and the locating hole in which the optical member is located by at least one of mechanically, physically, and thermally deforming the edge portion of the locating hole at a distal end face of the distal end portion.

17. An endoscope comprising:

an elongated insertion section having a distal end portion, the insertion section having on the distal end portion thereof a rigid portion body which has a locating hole in which at least one of an objective optical system and an illumination optical system, each having an optical member, is located, a holding portion which is formed by at least one of mechanically, physically, and thermally deforming an edge portion of the locating hole at a distal end face of the distal end portion and prevents the optical member from slipping off the locating hole is provided on the boundary between the optical member and the locating hole in which the optical member is located.

18. An endoscope according to claim 17, wherein the holding portion includes a protrusion on the edge portion of the locating hole which is mechanically deformed toward the optical member.

19. An endoscope comprising:

an elongated insertion section having a distal end portion, the insertion section having on the distal end portion thereof a rigid portion body which has a locating hole in which at least one of an objective optical system and an illumination optical system, each having an optical member, is located, at least one of the objective optical system and the illumination optical system includes a frame member which is located in the locating hole and has the optical member inserted in the frame member, and a fixing portion is provided such that the rigid portion body and the frame member are fixed together by welding on the boundary between the frame member and the locating hole in which the frame member is located.

20. An endoscope comprising:

an elongated insertion section having a distal end portion and a proximal end portion, the insertion section having on the distal end portion thereof a rigid portion body which has a locating hole in which at least one of an objective optical system and an illumination optical system, each having an optical member, is located, the rigid portion body includes a small-diameter hole which is smaller in diameter than the locating hole and is situated near the locating hole and in which a small-diameter rod of a holding pin, having the small-diameter rod and a spread portion on one end portion of the small-diameter rod, is located, the spread portion having a holding portion which retains the optical member pushed in on the proximal end side of the insertion section and a fixing portion which is melted and fused together with the rigid portion body.

21. An endoscope comprising:

an elongated insertion section having a distal end portion, the insertion section having on the distal end portion thereof a rigid portion body which has a locating hole in which at least one of an objective optical system and an illumination optical system, each having an optical member, is located, at least one of the objective optical system and the illumination optical system includes a frame member which is located in the locating hole and has the optical member inserted in the frame member, a fixing portion is provided such that the rigid portion body and the frame member are fixed together by welding on the boundary between the frame member and the locating hole in which the frame member is located, and a holding portion which prevents the optical member from slipping off the locating hole is provided by extending a molten metal formed by melting the frame member.

22. An endoscope according to claim 21, wherein the fixing portion and the holding portion are formed integrally with each other.

* * * * *